(12) United States Patent
McKay

(10) Patent No.: US 8,431,148 B2
(45) Date of Patent: Apr. 30, 2013

(54) BONE VOID FILLER

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 543 days.

(21) Appl. No.: 12/043,652

(22) Filed: Mar. 6, 2008

(65) Prior Publication Data

US 2008/0221511 A1  Sep. 11, 2008

Related U.S. Application Data

(60) Provisional application No. 60/893,838, filed on Mar. 8, 2007.

(51) Int. Cl.
  *A61F 2/00* (2006.01)
  *A61F 13/00* (2006.01)
  *A61F 2/28* (2006.01)

(52) U.S. Cl.
  USPC .................. 424/426; 424/422; 623/23.61

(58) Field of Classification Search .................... None
  See application file for complete search history.

(56) References Cited

U.S. PATENT DOCUMENTS

| | | | |
|---|---|---|---|
| 5,776,193 A * | 7/1998 | Kwan et al. ................ | 424/423 |
| 6,372,257 B1 | 4/2002 | Marchosky | |
| 6,376,573 B1 * | 4/2002 | White et al. ................ | 523/115 |
| 6,579,857 B1 * | 6/2003 | Lind et al. ................ | 514/46 |
| 2002/0055143 A1 * | 5/2002 | Bell et al. ................ | 435/69.1 |
| 2002/0110541 A1 | 8/2002 | Petersen | |
| 2003/0236573 A1 * | 12/2003 | Evans et al. ............... | 623/23.58 |
| 2005/0169956 A1 * | 8/2005 | Erbe et al. ................ | 424/423 |
| 2005/0214340 A1 | 9/2005 | Erbe | |
| 2006/0067971 A1 | 3/2006 | Story | |
| 2006/0067973 A1 | 3/2006 | Schachter | |
| 2006/0246150 A1 | 11/2006 | Thorne | |

FOREIGN PATENT DOCUMENTS

| EP | 1719531 A2 | 3/1998 |
|---|---|---|
| WO | 03071991 A1 | 9/2003 |

OTHER PUBLICATIONS

Jones, Alan L., Recombinant Human Bone Morphogenic Protein-2 in Fracture Care, J Orthop Trauma 2005; 19(Suppl.):S23-S25.*
Wang, Jwo-Lin, et al., The Assay of Bone Reaction after Implantation of Calcium Sulfate and A composite of Calcium Sulfate and Calcium Phosphate, Journal of Medical and Biological Engineering, 23 (4): 205-212.*
Legeros, R. Z., et al., Journal of Materials Science: Materials in Medicine, 14 (2003) pp. 201-209.*
Search Report for PCT/US2008/056169, Sep. 24, 2008.

* cited by examiner

*Primary Examiner* — Scott Long
*Assistant Examiner* — Lyndsey Beckhardt
(74) *Attorney, Agent, or Firm* — Sorell Lenna & Schmidt LLP

(57) ABSTRACT

A novel composition and kit for a bone void filler are provided. The improved bone void filler includes a porous, collagen scaffolding admixed with calcium phosphate and at least one stabilizer agent. Optionally, the bone void filler further includes at least one bioactive agent.

4 Claims, 4 Drawing Sheets

BONE VOID FILLER

CROSS-REFERENCE TO RELATED APPLICATIONS

This application claims the benefit of U.S. Provisional Patent Application No. 60/893,838 filed on Mar. 8, 2007.

FIELD OF THE INVENTION

The present invention relates to an improved bone void filler, which includes a porous, collagen scaffolding admixed with calcium phosphate and at least one stabilizer agent.

BACKGROUND OF THE INVENTION

The use of bone graft substitutes for treatment of bone injuries/illnesses is continuously expanding with an increasingly active and aging population. Among the clinical indications that bone graft substitutes are being used for are bone fractures, bone cysts, prosthetic joint revision procedures involving bone loss, avascular necrosis of the femoral head, spinal fusions due to degenerative disc disease, oral maxillofacial bone defects and reconstructions, and osteoporotic fractures. All these clinical indications may cause limited mobility and often, particularly in the elderly, can, in extreme cases, result in death. These clinical indications often require surgical bone grafting to prevent delayed or non-unions from occurring. Revision surgery should be avoided if possible because bone healing rates are typically lower after a delayed or non-union has developed. Therefore, effective bone graft substitutes are an important treatment option for repair of bone defects and fractures.

The major problem associated with bone regeneration is the lack of a suitable scaffolding materials which can retain its shape and stay within the bone defect during the healing process but which is also compatible with the body. Properties which the bone regeneration material should possess include biocompatibility, porosity, strength, cohesiveness, shape retention, durability, and elasticity, in order to facilitate consistent regeneration of bone in the desired location, amount, and volume. Therefore, such material must have approximately the same porosity and structure of normal bone, but must not be susceptible to over hydration and diffusion from the surgical site.

Current research is focused around the development of bone graft substances that can be easily packed into irregular bone defects and once implanted in place stay in a cohesive mass. The graft substance has an inherent cohesive consistency preventing it from becoming diluted with bodily fluids, such as blood, and losing its original implanted shape.

The use of carrier matrices to promote the formation of bone at a site in a patient is well known, and related products are currently available on the market, such as Mastergraft® Putty, by Medtronic Sofamor Danek (Memphis, Tenn.). These matrices are typically in the form of a relatively large, soft collagen sponge or dry cake. Before insertion into the target site, the sponge is wetted, usually with sterile water or bone marrow aspirated from the patient, at a ratio of about 1:1 to about 1:2 by volume. The bone marrow is permitted to soak into the scaffolding provided by the sponge, and the sponge is then kneaded by hand, thereby obtaining a pliable putty consistency that may subsequently be gently packed into the target site. The collagen in the sponge provides a malleable putty, non-water soluble carrier that permits accurate placement and retention of biological factors at the implantation site. However, if the surgeon over-manipulates the putty, or if there are excessive amounts of blood at the target site, the putty may lose some of its cohesiveness, which may cause some of the implant to flow out of the target site.

Accordingly, there is a need for improved bone void fillers suitable for repair of bone defects.

SUMMARY OF THE INVENTION

The instant invention addresses these and other needs in the art by providing, in one aspect, a bone void filler, which includes collagen, calcium phosphate, and at least one stabilizer agent. In one embodiment, the collagen provides about 5% to about 30% of the weight of the bone void filler; the calcium phosphate provides about 55% to about 94% of the weight of the bone void filler; the one or more stabilizer agents make up about 1% to about 15% of the weight of the bone void filler. This stabilizer agent provides increased cohesiveness of the putty in the presence of over hydrated conditions and or causes the putty to actually set-up. In one embodiment, the one or more stabilizer agents include calcium sulfate.

In another embodiment, the bone void filler may further include at least one bioactive agent. Suitable bioactive agents include growth factors, anti-inflammatory compounds, antibiotics, analgesic compounds, nucleic acid sequences, cells, and combinations thereof.

In another aspect, the instant invention provides a kit that includes a bone void filler. The bone void filler includes collagen, calcium phosphate, and at least one stabilizer agent. The kit also includes a set of instructions. In one embodiment, the dry weight of the collagen provides about 5% to about 30% of the weight of the bone void filler; the calcium phosphate provides between about 55% to about 94% of the weight of the bone void filler; and the stabilizer agent provides between about 1% to about 15% of the weight of the bone void filler. In one embodiment, the stabilizer agent includes calcium sulfate. Further, in an additional set of embodiments, the kit includes at least one bioactive factor. Suitable bioactive agents include growth factors, anti-inflammatory compounds, antibiotics, analgesic compounds, nucleic acid sequences, cells, and combinations thereof.

DETAILED DESCRIPTION OF THE INVENTION

An improved bone void filler, which includes a stabilizer agent is disclosed. In particular, one embodiment provides a bone void filler, which includes collagen, calcium phosphate, and a stabilizer agent.

The term "patient" refers to a biological system to which a treatment can be administered. A biological system can include, for example, an individual cell, a set of cells (e.g., a cell culture), an organ, or tissue. Additionally, the term "patient" can refer to animals, including, without limitation, humans.

Definitions

To aid in an understanding of the various disclosed embodiments, the following non-limiting definitions are provided:

The term "treating" or "treatment" of an injury or disease refers to executing a protocol, which may include administering one or more drugs, implants or the like to a patient (human or otherwise), in an effort to repair the bone injury or alleviate signs or symptoms of a disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

In one embodiment, a bone void filler may be in the form of a putty. Such a bone void filler includes collagen (10-30% by dry wt.) and calcium phosphate (55-89% by wt.). Preferably, the calcium phosphate is provided in granules having a diameter of between 0.1-5 mm, or, more preferably, 0.5-1.6 mm. The calcium phosphate may be provided in one or more chemical forms. In one embodiment, biphasic calcium phosphate is used. Optionally, the calcium phosphate may contain hydroxyapatite. In one embodiment, a biphasic calcium phosphate (BCP) bioceramic is used. BCP includes an intimate mixture of hydroxyapatite (HA), $Ca_{10}(PO_4)_6(OH)_2$, and beta-tricalcium phosphate (beta-TCP), $Ca_3(PO_4)_2$, in varying HA/beta-TCP ratios. In one embodiment the preferred HA/beta-TCP ratios are in the range of about 15/85 to about 25/75.

The composition of the collagen may also vary in different embodiments. In one embodiment, the collagen consists of a fibular collagen. Fibular collagen is precipitated collagen into highly organized relatively strong fibular strands during it's processing from digested collagen donor tissues such as skin and tendon.

In another set of embodiments, the collagen includes about 20-40% by weight of soluble collagen and about 60-80% by weight of a more organized insoluble form of fibular collagen. The soluble collagen may increase the flowability and cohesiveness of the bone void filler.

Figure 1:
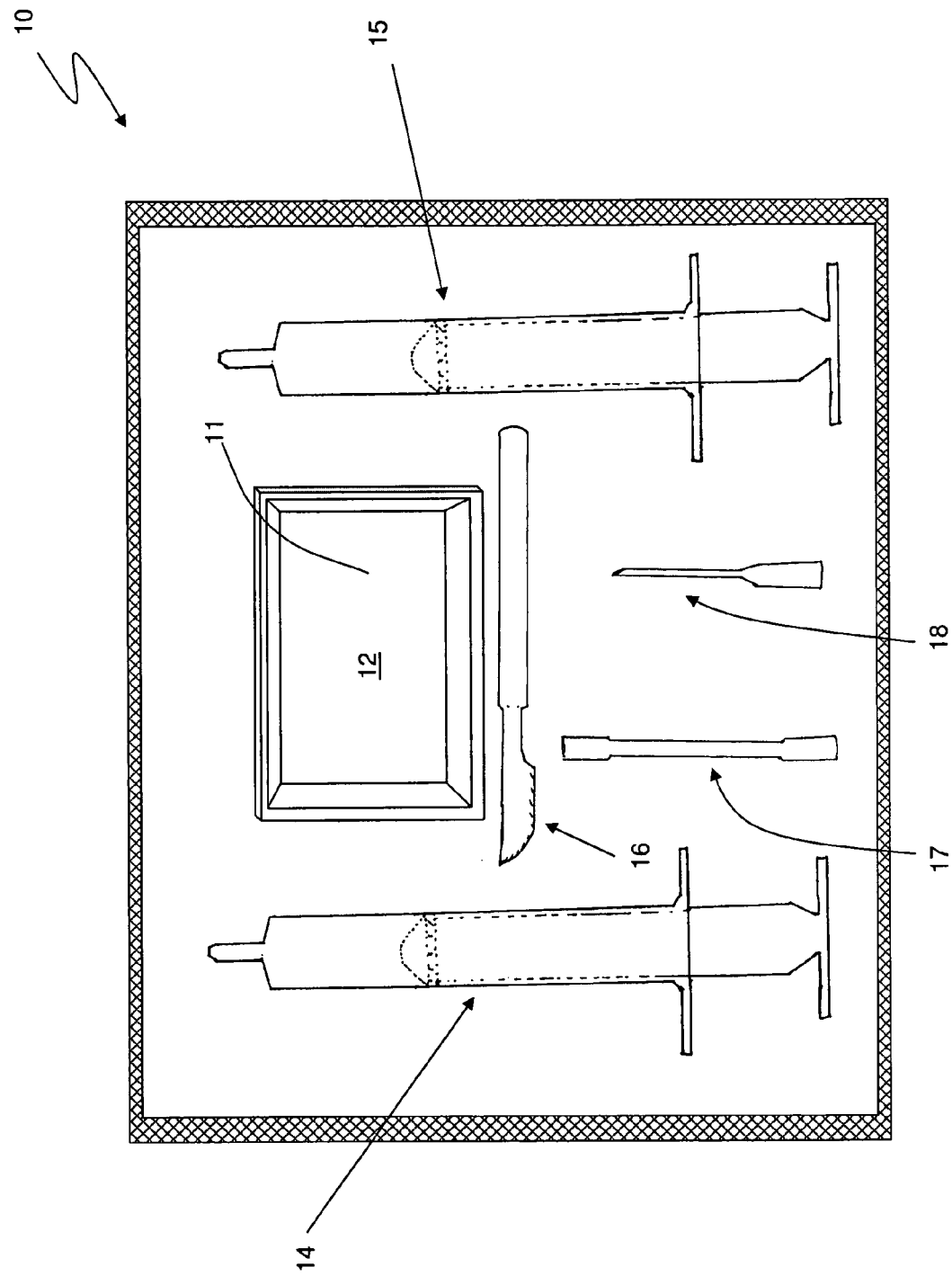
FIG. 1 shows an embodiment kit.
Figure 2:
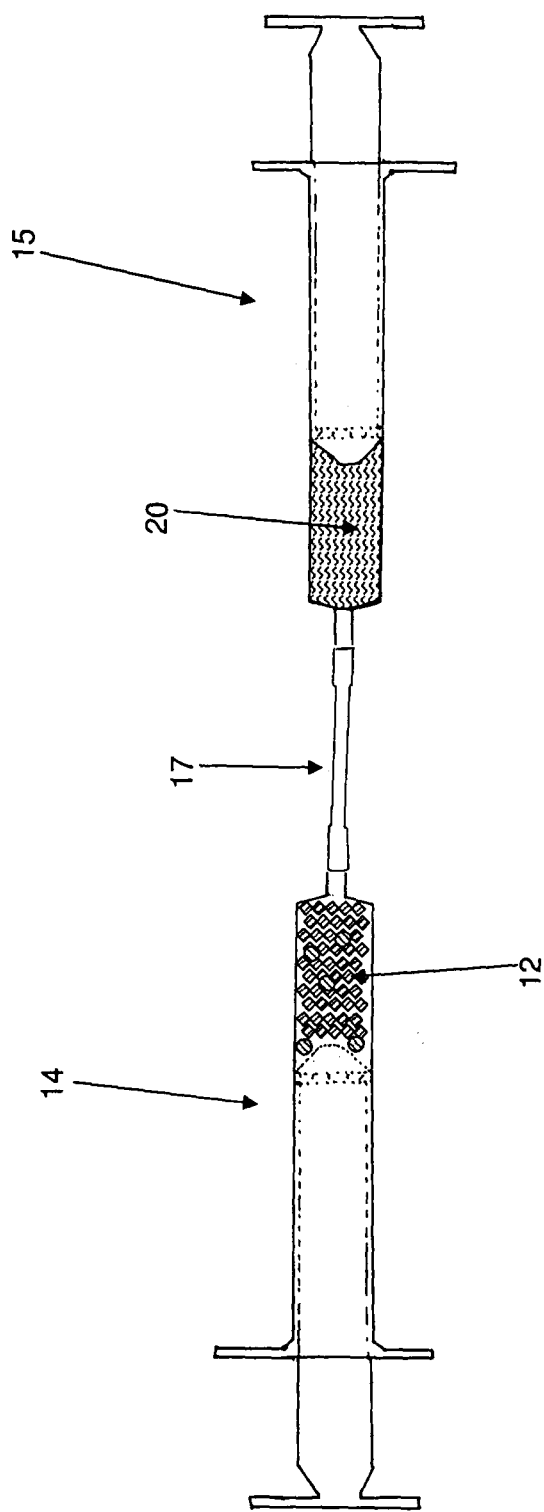
FIG. 2 shows hydrating an embodiment sponge.

As shown in FIG. 1, the collagen, admixed with the calcium phosphate, may be freeze dried (i.e., lyophilized) in the form of a sponge 12 within a kit 10 for packaging, shipment and storage. The kit 10 may further include, for example, syringes 14, 15 for hydrating the sponge 10 and delivering a resulting putty to a target site, a knife or like cutting means for optionally cutting the sponge 12 into smaller sections, a connection tube 17 for fluidly connecting together the syringes 14, 15, and a delivery device 18 that may be connected to one of the syringes 14, 15 and used to inject the putty into the target site. As shown in FIG. 2, the dehydrated sponge 12 may be removed from the packaging 10, optionally sectioned with knife 16, and disposed in a first syringe 14. Second syringe 15 may be filled with a suitable hydrating material 20, such as sterile water (optionally containing a bioactive agent, such as BMP-2 or rhBMP-2, an anti-inflammatory, analgesic, etc.), bone marrow aspirate, or the like. The syringes 14, 15 may then be connected together with connection tube 17, and then their respective contents may be driven back and forth to hydrate the sponge 12.

Alternatively, a surgeon may choose to simply manually hydrate and knead the sponge 12. In certain embodiments, the sponge 12 may be provided a concave or depressed surface 11. Concave or depressed surface 11 may serve as a reservoir that can accept the hydrating material 20, rather than using the second syringe 15. The hydrating material 20 may be allowed to soak within the concave or depressed surface 11, and a surgeon may subsequently knead the sponge 12 into a putty-like consistency.

Figure 3:
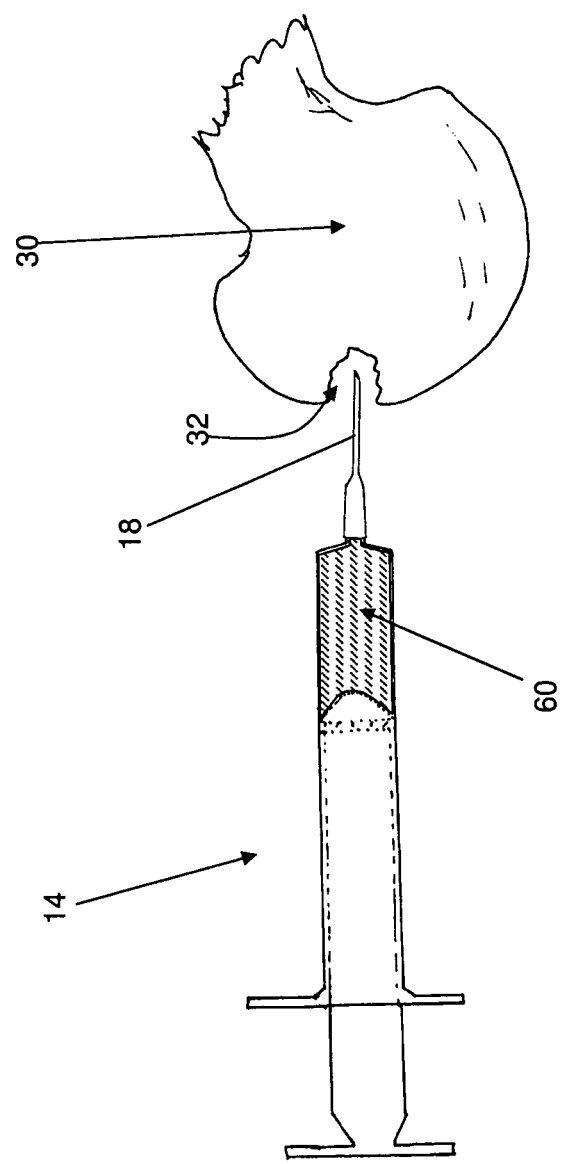
FIGS. 3 and 4 show an embodiment implant injected into a target site to fill a bone void.
Figure 4:
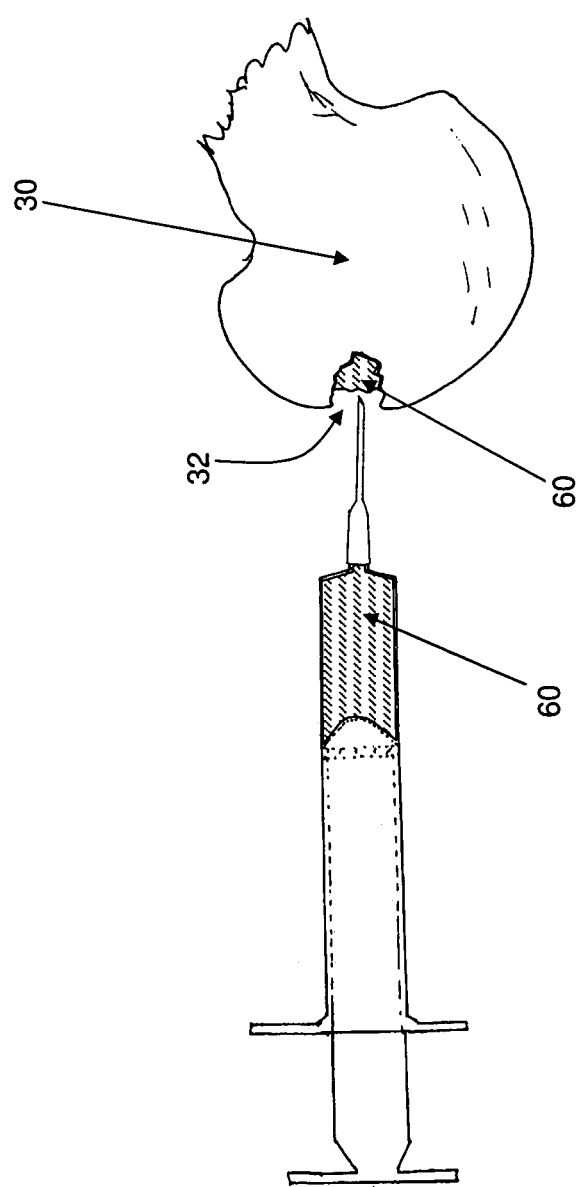

As shown in FIGS. 3 and 4, hydration of the collagen within the sponge 12 results in a flowable, putty-like material 60 that the surgeon can place into an irregular defect 32 in bone 30. For example, the surgeon may use the delivery device 18, connected to the first syringe 14, to inject the putty 60 into the defect 32; alternatively, the surgeon may manually apply the putty 60 to the defect 32. Without a stabilizer agent, however, this material 60 may continue to absorb blood leaching from the defect 32 and thereby lose some of its cohesiveness after placement into the surgical site 32; this may be particularly true if the surgeon over-manipulates the putty 60. The inventors have found that the addition of a stabilizer agent improves the cohesiveness of the putty material 60 under these extreme conditions, and, if desired, can cause the putty 60 to "set-up" in place, such as in the target site 32. In a preferred embodiment, the stabilizer agent is added to the putty at the time of manufacture so it is mixed in with the collagen and calcium phosphate and then freeze dried.

Suitable stabilizer agents include, without limitation, calcium sulfate, alginate, chitosan, hyaluronic acid, gelatin, fibrin, elastin, silk, or any combination of them. In one embodiment, the stabilizer agents are calcium-based agents with a reaction chemistry that provides cohesiveness or set-up properties. In a specific embodiment, the stabilizer agent is calcium sulfate. The amount of calcium sulfate added could vary between about 1% and about 15% of the bone void filler by dry weight (i.e., 1% and about 15% by weight of the dry sponge 12), with the preferred amount being between about 2% and about 5% by dry weight. A large amount (e.g., over about 15%) is not needed since the calcium sulfate will act to bind the fibular collagen strands together. After hydration, the calcium sulfate slowly reacts, holding the putty 60 in a cohesive mass that is less susceptible to blood diluting and washing the putty 60 out of the bone defect 32. The stabilizer agent may also make the material 60 less sticky to the surgeon's gloves, and may improve flowability of the putty 60 out of a syringe 14. By keeping the quantity of the calcium sulfate low, the bone void filler 60 maintains its porosity, thus allowing for rapid cell infiltration and bone formation.

A person of ordinary skill in the art will appreciate that the methods of preparing the bone void filler of the instant invention are known in the art. The compounds for the bone void filler may be commercially purchased. For example, calcium sulfate may be obtained from Noah Technology Corp. (San Antonio, Tex.). A suitable mixture of the fibular collagen, the soluble collagen and the calcium phosphate may be obtained in the form of the MASTERGRAFT® Putty supplied by Medtronic Sofamor Danek, Inc. (Memphis, Tenn.). Alternatively, the fibular collagen, the soluble collagen and the calcium phosphate may be obtained separately. For example, kit 10 may include the stabilizer agent separately from the sponge 12 so that a surgeon may optionally mix in a suitable amount of the stabilizer when hydrating the sponge 12 to form the putty 60.

MASTERGRAFT® Putty is supplied as a boat-shaped dry cake and comes in 5 volumes i.e., 0.75 cc, 1.5 cc, 3 cc, 6 cc, and 9 cc. MASTERGRAFT® Putty may be hydrated with sterile water or bone marrow aspirate. The sterile water solution, which may further include a growth factor, such as BMP-2 is slowly absorbed by the cake and once all solution is absorbed is manually kneaded into a putty consistency. The at least one stabilizer agent (e.g., calcium sulfate) is preferably added at the time of manufacturing the sponge 12. To form the sponge 12, the stabilizer agent may be dissolved and blended with the collagen and the calcium phosphate. The resulting composition may then be freeze-dried into the desired shape to form the sponge 12. This embodiment of making the bone void filler may ensure a more uniform mixture of the components. Prior to surgery, the freeze-dried material 12 is wetted with a solvent 20 (e.g., water, saline, or a bone marrow aspirate), which may optionally contain at least one bioactive agent, to form a viscous mass 60 which can be injected or manually packed into the patient's bone void 32.

A person of the ordinary skill in the art would appreciate that the bone void filler of the instant invention also allows for optimal loading of its porous structure with bioactive agents, such as, for example, growth factors or cells. Suitable bioactive agents include, without limitation, growth factors (including osteogenic and chondrogenic agents), anti-inflammatory agents, pain-reducing agents, antibiotics, cells, nucleic acid sequences, and any combinations thereof.

Growth factors suitable for use in the practice of the invention include but are not limited to bone morphogenic proteins, for example, BMP-2, rhBMP-2, BMP-4, rhBMP-4, BMP-6, rhBMP-6, BMP-7-[OP-1], rhBMP-7, GDF-5, and rhGDF-5, as disclosed, for example, in the U.S. Pat. Nos. 4,877,864; 5,013,649; 5,661,007; 5,688,678; 6,177,406; 6,432,919; 6,534,268, and 6,858,431, and in Wozney, J. M., et al. (1988) Science, 242(4885):1528-1534. In one embodiment, the bone void filler contains an effective amount of a BMP-2 protein, an rhBMP-2 protein, functional fragments thereof, or combinations thereof.

Suitable antibiotics include, without limitation nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol or any combination thereof.

Suitable anti-inflammatory compounds include both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluocinolone, fluradrenolone acetonide, medrysone, amcinafel, amcinafide, betamethasone and the balance of its esters, chloroprednisone, chloroprednisone acetate, clocortolone, clescinolone, dichlorisone, difluprednate, fluclorinide, flunisolide, fluorometholone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds may also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

The various compounds encompassed by anti-inflammatories are well-known to those skilled in the art. For detailed disclosure of the chemical structure, synthesis, side effects, etc. of non-steroidal anti-inflammatory compounds, reference may be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974), each incorporated herein by reference.

Mixtures of these non-steroidal anti-inflammatory compounds may also be employed, as well as the pharmacologically acceptable salts and esters of these compounds.

In addition, so-called "natural" anti-inflammatory compounds may be useful. Such compounds may suitably be obtained as an extract by suitable physical and/or chemical isolation from natural sources (e.g., plants, fungi, by-products of microorganisms). Suitable non-limiting examples of such compounds include candelilla wax, alpha bisabolol, aloe vera, Manjistha (extracted from plants in the genus *Rubia*, particularly *Rubia Cordifolia*), and *Guggal* (extracted from plants in the genus *Commiphora*, particularly *Commiphora Mukul*), kola extract, chamomile, sea whip extract, compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate.

Generally, anti-inflammatory non-steroidal drugs are included in the definition of pain-reducing agents because they provide pain relief. In addition, suitable pain-reducing agents include other types of compounds, such as, for example, opioids (such as, for example, morphine and naloxone), local anaesthetics (such as, for example, lidocaine), glutamate receptor antagonists, α-adrenoreceptor agonists, adenosine, canabinoids, cholinergic and GABA receptors agonists, and different neuropeptides. A detailed discussion of different analgesics is provided in Sawynok et al., (2003) *Pharmacological Reviews*, 55:1-20, the contents of which are incorporated herein by reference.

Suitable cells include, without limitations, stem cells, e.g., embryonic or adult stem cells, which can conveniently be derived from the blood or bone marrow of the patient or from an allogeneic source, which preferably is immunologically compatible with the patient. Other suitable cells may include chondrogenic or osteogenic precursor cells. A person of the ordinary skill in the art will appreciate that the cells may be genetically modified (e.g., overexpressing certain proteins, or having expression of certain proteins inhibited). Methods of creating such genetically modified cells are within knowledge and expertise of the person of ordinary skill in the art.

Suitable nucleic acid sequences include, without limitation, cDNA sequences encoding the at least one bioactive factor of a proteinaceous nature. These cDNAs may be included within respective vectors (e.g., AAV). In another embodiment, the nucleic acid sequences may be siRNAs or shRNAs or nucleic acid sequences encoding for such siRNAs or shRNAs. These siRNAs and shRNAs may be used in embodiments wherein it is desirable to inhibit expression of certain genes, such as, for example inflammatory protein genes such as TNF, IL-1, IL-6, and BMP inhibitor proteins such Noggin and Chordin, and intracellular BMP inhibitors SMADS. A person of ordinary skill in the art will appreciate that the nucleotide sequences for such genes are available in publicly-accessible databases, including, without limitation, Genbank. Further, the criteria for the siRNA selection have been also described in the art. Accordingly, a person of ordinary skill in the art will have sufficient knowledge and expertise in preparing such siRNAs or shRNAs.

The methods of incorporating the at least one bioactive factor are also known in the art. In one embodiment, the bone void filler 12 may be soaked in a solution of the at least one bioactive factor before implantation. In some embodiments, depending on the properties of the at least one bioactive factor, the bone void filler may be soaked in the solution for 1-60 minutes before the implantation. The at least one bioactive factor may also be dripped, brushed, or sprayed onto the bone void filler of the instant invention.

If the at least one bioactive factor includes cells, the cells may be re-suspended in a volume of media (e.g., Dulbecco's Modified Eagle's Medium) and cultured with the bone void filler of the instant invention. Due to the properties of the surface of the bone void filler and the porosity of the bone void filler, the cells will populate the external surfaces of the bone void filler and its internal voids. Optimal loading conditions (e.g., medium composition, shaking, if necessary) may be easily determined by the person of ordinary skill in the art. Further, the bone void filler may be wetted with an aspirate from the patient's bone marrow, thus allowing the bone marrow cells to populate the voids and pores within the bone void filler.

The kit 10 including the bone void filler according to any of the embodiments described above may further include a set of instructions. Optionally, if the supplied bone void filler 12 does not include the at least one bioactive agent, the kit 10 may be separately supplied with the at least one bioactive agent. Such embodiments may be preferable, since the storage conditions for the bone void filler 12 and the at least one bioactive factor may differ.

The set of instructions includes information for safe and effective preparation and use of the kit. For example, the information may include guidelines for delivery of the bone void filler and for the incorporation of the at least one bioactive factor into the bone void filler. A person of ordinary skill in the art will appreciate that the set of instruction may be provided is multiple formats, including, without limitations, written instructions, audiorecording, videorecording, digital media, and a combination thereof.

In certain aspects, the bone void fillers as described herein can be delivered in spinal fusion applications such as interbody fusions, oral maxillofacial applications such as ridge augmentation, the repair of cranial defects, iliac crest backfilling, acetabular defects, and in the repair of tibial plateau and long bone defects. Such methods can be used to treat major or minor defects in these or other bones caused by trauma (including open and closed fractures), disease, or cogenital defects, for example.

Every patent and non-patent publication cited in the instant disclosure is incorporated into the disclosure by reference to the same effect as if every publication is individually incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A bone void filler comprising collagen, calcium phosphate, an effective amount of BMP-2 or a functional fragment thereof and at least one stabilizer agent comprising calcium sulfate, wherein: a dry weight of said collagen is between about 5% and about 30% of the weight of the bone void filler and said collagen comprises soluble collagen, and insoluble fibular collagen comprising collagen strands, wherein a dry weight of the soluble collagen is between about 20% and about 40% of the dry weight of the collagen; and a dry weight of the insoluble fibular collagen is between about 60% and about 80% of the dry weight of the collagen;

a weight of said calcium phosphate is between about 55% and about 94% of the weight of the bone void filler and the calcium phosphate is provided in granules having a diameter of between 0.1 and 5 mm and the calcium phosphate comprises hydroxyapatite and tricalcium phosphate in a weight ratio of hydroxyapatite: tricalcium phosphate of about 15:85 to about 25:75; and a weight of said at least one stabilizer agent is between about 1% and about 15% of the weight of the bone void filler, wherein the filler is in the form of a putty and the stabilizer binds collagen strands together.

2. The bone void filler of claim 1, wherein a weight of said at least one stabilizer agent is between about 2% and about 5% of the weight of the bone void filler.

3. The bone void filler of claim 1, wherein the bone void filler provides a porous structure.

4. The bone void filler of claim 1, wherein the granules have a diameter of 0.5-1.6 mm.

* * * * *